United States Patent [19]

Snyder

[11] 4,261,203

[45] Apr. 14, 1981

[54] TIP FOR SOIL GAS PROBE

[75] Inventor: Vona L. Snyder, Bartlesville, Okla.

[73] Assignee: Phillips Petroleum Company, Bartlesville, Okla.

[21] Appl. No.: 12,786

[22] Filed: Feb. 16, 1979

[51] Int. Cl.³ .............................................. G01N 1/22
[52] U.S. Cl. ................................... 73/421.5 R; 73/425; 175/21; D15/139
[58] Field of Search ................... 73/421.5 R; 173/91; 175/21, 20, 19; 219/237; D15/139

[56] References Cited

U.S. PATENT DOCUMENTS

| 216,042 | 6/1879 | Le Grand et al. | 175/19 |
|---|---|---|---|
| 1,845,709 | 2/1932 | Haddon | 175/20 |
| 3,050,095 | 8/1962 | Prather | 173/91 |
| 3,084,553 | 4/1963 | Cullinan et al. | 175/21 X |
| 3,087,560 | 4/1963 | Dodson | 175/19 X |
| 3,198,265 | 8/1965 | Voelkerding | 173/74 |
| 3,238,784 | 3/1966 | Dorsey et al. | 73/425 |
| 3,307,912 | 3/1967 | Davis | 23/232 |
| 3,313,356 | 4/1967 | Clevenger | 173/91 |
| 3,490,288 | 1/1970 | Patnode | 73/421.5 |
| 3,835,710 | 9/1974 | Pogorski | 73/421.5 R |
| 4,020,697 | 5/1977 | Jander | 73/421.5 R |

Primary Examiner—Daniel M. Yasich

[57] ABSTRACT

A tip terminating in a conical point at its lower end and having a plurality of gripping sides is provided for movable mounting on a soil gas probe.

2 Claims, 7 Drawing Figures

TIP FOR SOIL GAS PROBE

BACKGROUND OF THE INVENTION

This invention relates to an apparatus for detecting subsurface accumulations of gases, for example helium, which may be indicative of nearby hydrocarbon deposits or deposits of radioactive ores. In another aspect, the invention relates to a tip for use on such an apparatus.

In order to take a subsurface gas sample which is representative of the gases present, it is necessary to prevent atmospheric air from contaminating the subsurface sample. This is accomplished by driving a shaft into the earth, the dimensions of the shaft being such that it fills the cavity made as it is driven into the earth. A gas seal formed by the exterior wall of the shaft and the surrounding earth prevents contamination of the sample by atmospheric air. After the shaft has been driven to the desired depth, an aperture near the lower end of the shaft is exposed and the gas sample taken.

The design of the tip of the gas probe is important. If the largest cross-sectional dimension of the tip is greater than the largest cross-sectional dimension of the probe, the probe will not fill the cavity made in the earth by the tip and atmospheric air will contaminate any gas samples collected. For that reason, the tip should not have a greater diameter than the shaft of the probe. In devices wherein the shaft is partially unscrewed from the tip to expose the sampling aperture, the tip must be designed so as to resist rotation in the earth as the shaft is being partially unscrewed therefrom. In the past this was accomplished by utilization of fins on the tip or a wedge-shaped tip. Fin-like protrusions on the tip as in U.S. Pat. No. 3,198,265 caused excessive disturbance of the soil around the shaft and at least partially destroyed the gas seal between the soil and the shaft. The fins also sometimes made removal of the shaft from the earth extremely difficult. Wedge-shaped tips as in U.S. Pat. No. 3,835,710 are difficult to drive into hard earth or earth containing rocks. This is due to the relatively large area of the leading edge of the wedge. The poor penetration of the wedge- or chisel-shaped point causes excessive stresses in apparatuses which utilize these points and frequently results in premature parts failure.

OBJECTS OF THE INVENTION

It is thus an object of the present invention to provide a tip for a soil gas probe characterized by good penetrating abilities.

It is another object of this invention to provide a tip for a soil gas probe which is durable and rugged.

It is a further object of this invention to provide a tip for a soil gas probe which reduces operating stresses on the soil gas probe and is well adapted for its intended purpose.

Other aspects, objects and the several advantages of the invention will be readily apparent to one skilled in the art from the following disclosure and the appended claims.

SUMMARY OF THE INVENTION

In accordance with the present invention, a tip having an upper end and a lower end, with a conical point at the lower end and a plurality of soil gripping sides intermediate the lower end and the upper end, is provided for a soil gas probe. Also provided is a soil gas probe utilizing the tip.

BRIEF DESCRIPTION OF THE DRAWINGS

FIGS. 5, 6 and 7 are reduced scale from FIGS. 2, 3 and 4.

Referring to FIG. 1, the reference numeral 1 designates generally a preferred embodiment of an apparatus for withdrawing subsurface gas samples. The apparatus 1 is symmetrical and generally cylindrical in shape.

Figure 1:
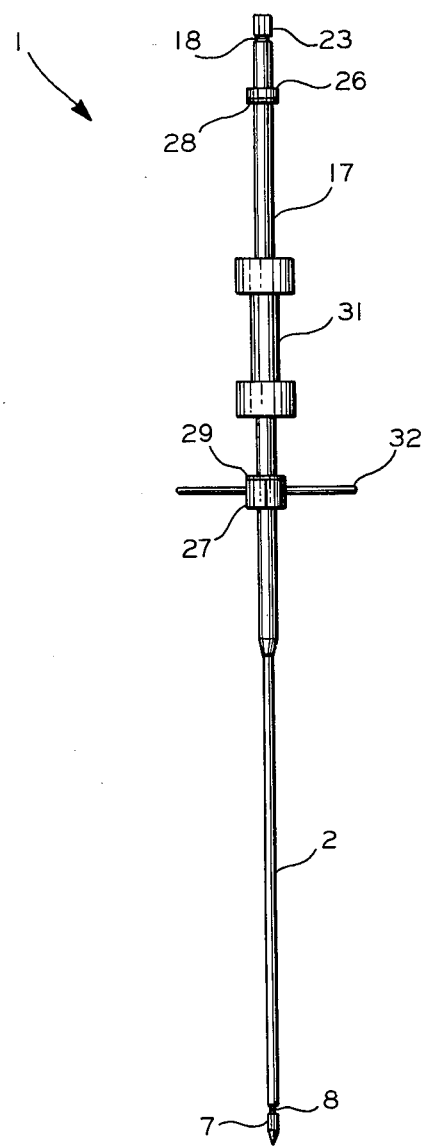
FIG. 1 is an elevated view of a soil probe adapted to use the tip of the present invention.

The apparatus 1 is comprised of a hollow shaft 2 which is adapted for being driven into the earth. The shaft 2 is preferably constructed of a rigid material, such as carbon steel, and is preferably of a constant circular cross section. The shaft 2 can be of any suitable length, preferably 1 to 10 feet.

An interior cavity 3 of the shaft 2 houses means for conveying gases from one end of the shaft 2 to the other. As best illustrated in FIGS. 4-7, the means for conveying gases comprises a tube 4. The tube 4 is preferably constructed of a resilient material which is relatively impervious to the types of gases being sampled. It has been found that silicon rubber tubing is particularly well suited. Because it is desirable to minimize dead air space within the conveying means, the inside diameter of the tube 4 is preferably no more than about 1 mm.

A lower end of tube 4 is in communication with an inlet port 6. Inlet port 6 is located adjacent the lower end of the shaft 2 and is adapted for initially receiving sample gases into the apparatus 1. A tip 7 is also located adjacent the lower end of the shaft 2. The tip 7 is movably mounted adjacent the lower end of the shaft 2 so as to be movable from a first position which closes the inlet port 6 from the exterior of the apparatus 1 to a second position in which the inlet port 6 is open to the exterior of apparatus 1.

Figure 4:
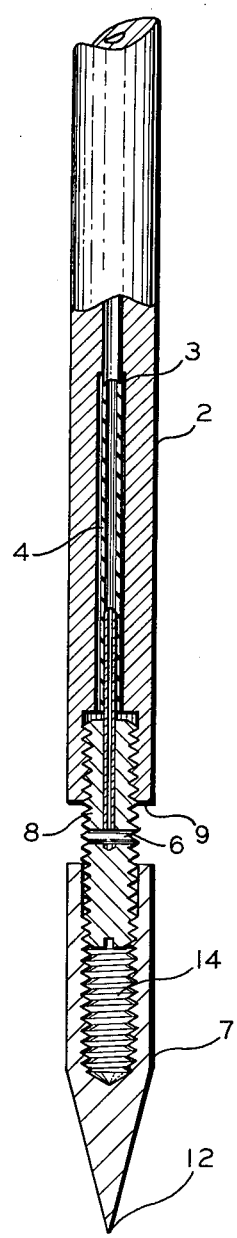
FIG. 4 is an enlarged view in partial cross section of a lower portion of the soil gas probe shown in FIG. 1.

As best illustrated in FIG. 4, the inlet port 6 is through the side wall of a coupling means 8, although it will be understood by those skilled in the art that the inlet port 6 can have other locations, for example through a lower face 9 of the shaft 2, it being essential only that the inlet port 6 be located near the bottom of the apparatus 1 and be adapted for being covered and uncovered by the tip 7. The coupling means 8 has a passage therethrough for flow communication between the inlet port 6 and the tube 4. The coupling means 8 is secured to the lower end of the shaft 2 by any suitable means. As illustrated, the coupling means 8 is threadably secured to the lower end of the shaft 2.

Figure 2:
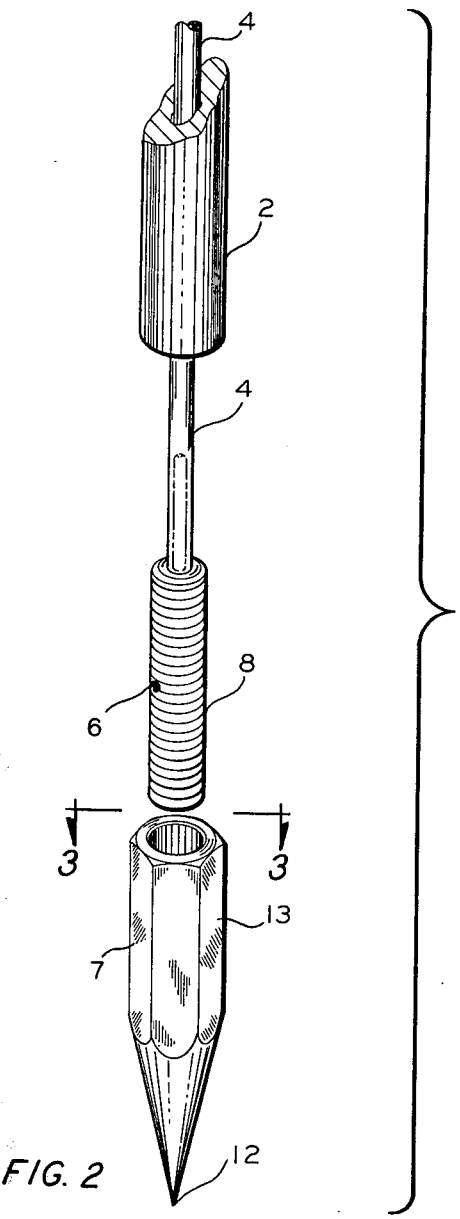
FIG. 2 depicts the tip of the soil gas probe in an enlarged perspective exploded view of a lower portion of the soil gas probe shown in FIG. 1.
Figure 3:
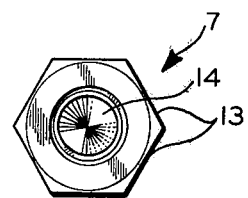
FIG. 3 is an enlarged plan view of the tip depicted in FIG. 2.

The tip 7 is adapted for being movably mounted adjacent the lower end of the shaft 2. The tip 7 has an upper end and a lower end with a conical point 12 at the lower end thereof and, as shown in FIGS. 2 and 3, a plurality of gripping sides 13 intermediate the upper end and the lower end defining a gripping portion of the tip. Preferably, the plurality of gripping sides 13 are adjacent the upper end of the tip 7. The point 12 is preferably needle sharp with an angle of divergence of from 25-35°. The plurality of gripping sides 13 preferably is between 3 and 12, more preferably 6, because of the ready availability of hexagonal stock from which tip 7 can be constructed. The largest cross-sectional dimension of the tip 7 should be no larger than the largest cross-sectional dimension of the shaft 2, to avoid interference with the gas seal formed by the earth around the shaft 2 when the apparatus is being utilized. The gripping sides 13 are preferably flat. The tip 7 preferably has a regular polygonal cross section through its gripping portion. In this embodiment, the only radial projections from the body of the tip 7 are the vertices of the regular polygonal cross section. The tip 7 is preferably constructed from a durable material. A preferred embodiment is machined from hexagonal 4140 steel stock.

The tip 7 is threadably mounted adjacent the lower end of the shaft 2 by the coupling means 8. Preferably, coupling means 8 engages with a tapped lower portion of an interior cylincdrical surface defining an axial bore 14 partially extending through the tip 7 from the upper end. An upper portion of the axial bore 14 can be free-bored or left untapped as best illustrated in FIG. 4 to facilitate flow of gases from the exterior of the apparatus 1 to inlet port 6 when contact between tip 7 and shaft 2 is broken. By partially unscrewing the shaft 2 from the tip 7, the inlet port 6 is exposed to the exterior of the apparatus 1.

Figure 7:
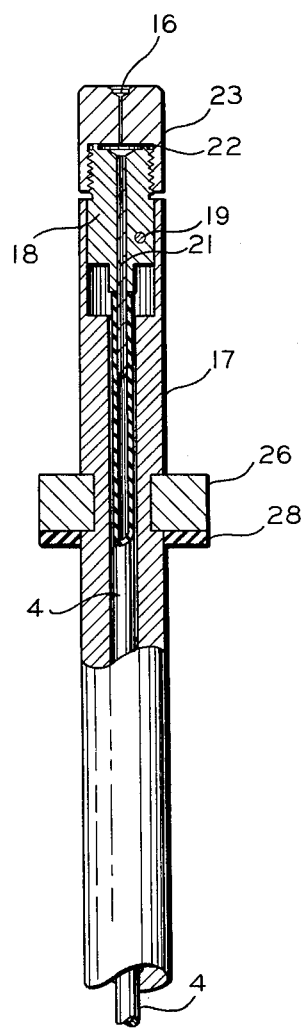

As shown in FIG. 7, the upper end of the tube 4 is secured to a septum holder 18. The septum holder 18 has a passage 21 therethrough, said passage being in flow communication with tube 4. Passage 21 is blocked from the exterior of the apparatus 1 by a puncturable septum 22 located across the passage 21 in an upper portion of the septum holder 18. Puncturable septum 22 is retained in position across passage 21 by a septum cap 23, which has an outlet port 16 therethrough. Septum cap 23 can be retained in position on septum holder 18 by any suitable means. As illustrated, septum cap 23 is threadably secured to septum holder 18.

Figure 5:
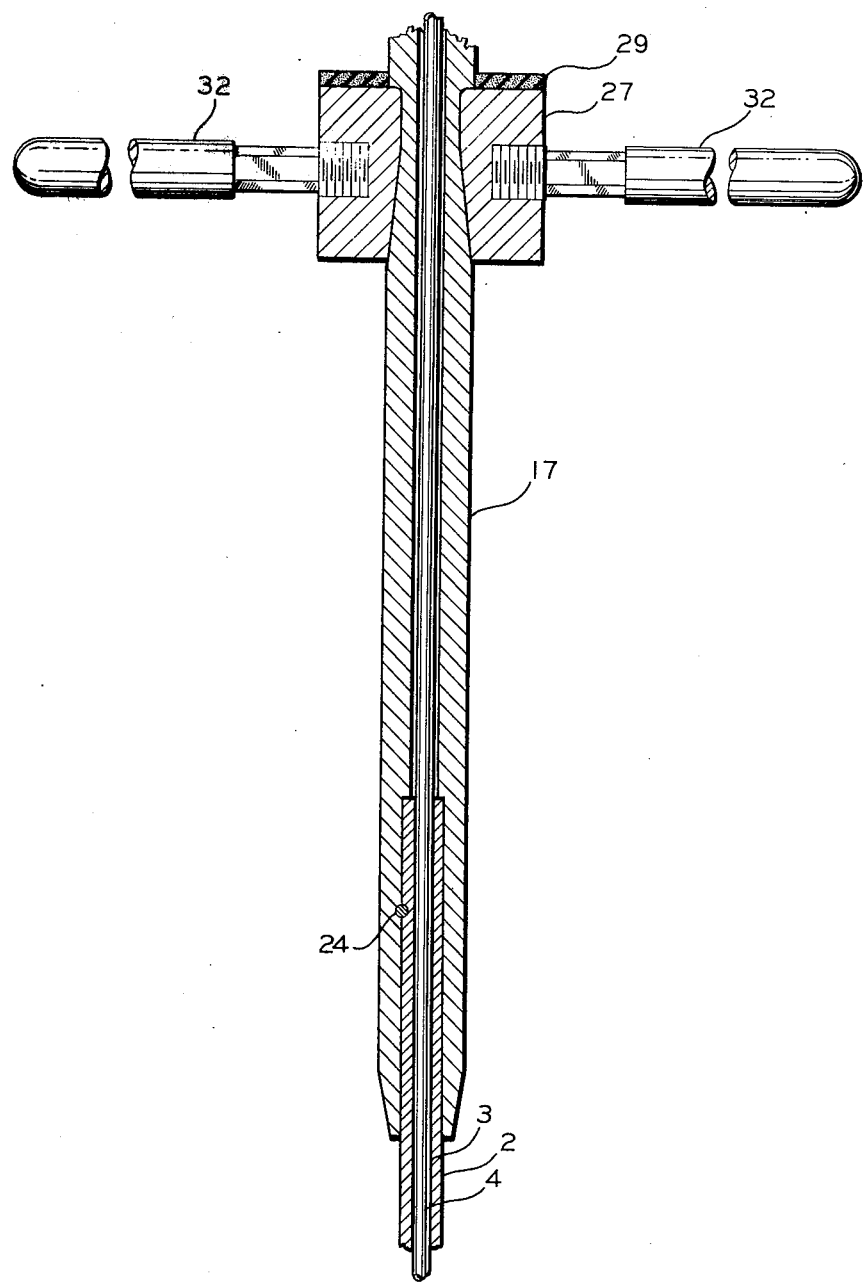
FIGS. 5, 6 and 7 are enlarged fragmented elevational views in partial cross sections of upper portions of the soil gas probe of FIG. 1.
Figure 6:
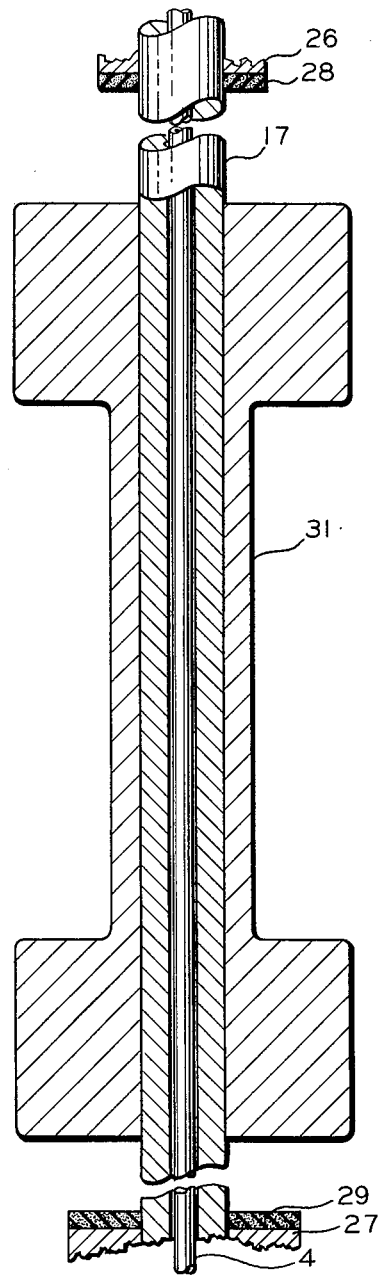

A hollow body 17 can be suitably secured to the shaft 2 and the septum holder 18 by means such as pins 19 and 24. Preferably, as shown in FIG. 5, at reduced scale from FIGS. 2, 3 and 4, the hollow body 17 at least partially encases the shaft 2. The body 17 is of a larger diameter than the shaft 2 and provides reinforcement to the shaft 2. As shown best by FIG. 6, the body 17 has an upper collar 26 and a lower collar 27 fixedly mounted thereon. Preferably, the collars are of a split construction for easy installation. Between the upper collar 26 and the lower collar 27 are located an upper gasket 28 and a lower gasket 29. The gaskets are preferably constructed of a resilient material such as rubber. A hammer 31 is slidably mounted on body 17 between upper gasket 28 and lower gasket 29. One or more handles 32 can also be provided, mounted fixedly on lower collar 27.

To utilize the apparatus 1, the tip 7 is first threaded firmly against the lower end of the shaft 2. The apparatus 1 is the positioned vertically over the location from which a sample of subsurface gas is desired. The tip 7 and shaft 2 are driven into the ground by sliding the hammer 31 repetitively aginst the lower gasket 29. The lower gasket 29 rests against the lower collar 27, thereby providing a hammering surface for the hammer 31. After the tip 7 has been driven to a desired depth, the shaft 2 is partially unscrewed away from the tip 7 by rotation with aid of the handles 32. The tip 7 remains stationary in the ground as the shaft 2 is partially screwed away. This procedure exposes the inlet port 6 to subsurface gases. The subsurface gases flow through the inlet port 6, through the coupling means 8, up to tube 4 to setpum holder 18 where the flow of gases is stopped by septum 22. Suitable withdrawing means such as are disclosed in U.S. Pat. No. 3,875,710 for example are inserted through the outlet port 16 puncturing the septum 22 to withdraw a sample of subsurface gas. The withdrawing means are then removed from the apparatus 1, and the apparatus is withdrawn from the earth by lifting with handles 32 or by being driven out by the impact of slidable hammer 31 on upper gasket 28 and upper collar 26.

It is to be understood that while there has been illustrated and described certain forms of this invention, it is not to be limited to the specific form or arrangement of parts herein described and shown, except to the extent that such limitations are found in the claims.

What is claimed is:

1. In a soil gas probe comprising:
   (a) a hollow shaft having a first end and a second end;
   (b) a hollow tube within the hollow shaft extending from the first end to the second end of the hollow shaft;
   (c) a coupling means mounted to one end of the hollow shaft having a threaded exterior surface and a passage therethrough with one end of the passage being in communication with one end of the hollow tube and the other end of the passage opening into an inlet port on the exterior surface of the coupling means;
   (d) means for selectively sealing the other end of the hollow tube;
   (e) an elongated hollow body encasing at least a portion of the hollow shaft;
   (f) a handle mounted on the elongated hollow body; and
   (g) a hammer slidably mounted on the elongated hollow body; the improvement comprising a tip having an upper end and a lower end and a largest cross sectional dimension which is no larger than the largest cross sectional dimension of the hollow shaft with a conical point at the lower end having an angle of divergence of from about 25 to about 35 degrees and six flat gripping sides adjacent the upper end defining a gripping portion of the tip having a regular hexagonal cross section with vertices projecting radially from the body of the tip and extending from the upper end along the gripping portion of the tip, the tip having a generally cylindrical interior surface with an upper untapped portion and a lower tapped portion defining an axial bore partially extending through the tip from the upper end, the tip being threadably mounted by the lower tapped portion of its generally cylindrical interior surface to the threaded exterior surface of the coupling means and being movable from a first position closing the inlet port to a second position opening the inlet port.

2. An apparatus as in claim 1 wherein said means for selectively sealing the other end of the hollow tube comprises a puncturable septum sealing the other end of said hollow tube.

* * * * *